United States Patent [19]

Hymes

[11] 4,274,420
[45] * Jun. 23, 1981

[54] MONITORING AND STIMULATION ELECTRODE

[75] Inventor: Alan C. Hymes, Hopkins, Minn.

[73] Assignee: LecTec Corporation, Eden Prairie, Minn.

[*] Notice: The portion of the term of this patent subsequent to Nov. 14, 1995, has been disclaimed.

[21] Appl. No.: 950,625

[22] Filed: Oct. 12, 1978

Related U.S. Application Data

[63] Continuation-in-part of Ser. No. 849,405, Nov. 7, 1977, Pat. No. 4,125,110, which is a continuation of Ser. No. 785,225, Apr. 6, 1977, abandoned, which is a continuation of Ser. No. 635,008, Nov. 25, 1975, abandoned.

[51] Int. Cl.³ .............................................. A61B 5/04
[52] U.S. Cl. .................................... 128/641; 128/798
[58] Field of Search ............................ 128/639–641, 128/644, 798, 783, 802, 803

[56] References Cited

U.S. PATENT DOCUMENTS

| | | | |
|---|---|---|---|
| 1,631,265 | 6/1927 | Harris | 260/760 |
| 1,777,162 | 9/1930 | Biddle | 106/79 |
| 2,555,037 | 5/1951 | Jensen | 128/639 |
| 2,943,627 | 7/1960 | Howell | 128/798 |
| 3,027,333 | 3/1962 | Friedman | 128/639 X |
| 3,547,105 | 12/1970 | Paine | 128/640 |
| 3,607,788 | 9/1971 | Adolph | 128/640 X |
| 3,665,064 | 5/1972 | Mosier et al. | 128/639 X |
| 3,720,209 | 3/1973 | Bolduc | 128/639 |
| 3,911,906 | 10/1975 | Reinhold, Jr. | 128/641 |
| 3,989,050 | 11/1976 | Buchalter | 128/803 X |
| 3,993,049 | 11/1976 | Kater | 128/640 |
| 3,998,215 | 12/1976 | Anderson et al. | 128/641 |
| 4,002,221 | 1/1977 | Buchalter | 128/660 X |
| 4,016,869 | 4/1977 | Reichenberger | 128/640 |
| 4,125,110 | 11/1978 | Hymes | 128/641 |

FOREIGN PATENT DOCUMENTS

| | | | |
|---|---|---|---|
| 675494 | 12/1963 | Canada | 128/641 |
| 410009 | 5/1934 | United Kingdom | 128/641 |
| 1299449 | 12/1972 | United Kingdom | 128/641 |

OTHER PUBLICATIONS

Nasa Tech. Brief, by Mosier, TSP69-10598, Nov. 1969.

Primary Examiner—Lee S. Cohen
Attorney, Agent, or Firm—Merchant, Gould, Smith, Edell, Welter & Schmidt

[57] ABSTRACT

An improved combination electrode for use in monitoring and stimulation medical applications is provided having an electrical current conductor including a connector plug and a skin-interfacing substrate material, this substrate being a composition including a karaya gum matrix containing an electrically conductive substance.

15 Claims, 4 Drawing Figures

MONITORING AND STIMULATION ELECTRODE

BACKGROUND OF THE INVENTION

The present application is a continuation-in-part of U.S. patent application, Ser. No. 849,405, filed Nov. 7, 1977 entitled "Monitoring and Stimulation Electrode" now U.S. Pat. No. 4,125,110 which is a continuation of U.S. patent application, Ser. No. 785,225, filed Apr. 6, 1977 entitled "Monitoring and Stimulation Electrode" (now abandoned) which was a continuation of U.S. patent application, Ser. No. 635,008, filed Nov. 25, 1975 entitled "Monitoring and Stimulation Electrode" (now abandoned).

Medical electrodes have in the past taken many shapes and forms. Principally, they have been shaped according to the use for which they are intended. Electrodes used in monitoring apparatus, such as EKG and EEG machines, commonly have small round contact surfaces. While electrodes used in such stimulation apparatus as pain control tend to be larger and have most often rectangularly or other surgical conveniently shaped contact surfaces. Electrodes used for grounding cautery tend to be larger in size. Whether intended for monitoring or stimulation use or as a ground use, a design objective for each electrode group has been, and continues to be, good electrical signal transmission between a patient's skin surface and the electrical wiring connected to a particular piece of apparatus. Not only is efficient signal transmission across the epidurum-conductor interface desirable, but so is effective signal transmission which is substantially free of current concentration points and electrical "feed back" (i.e. battery effect).

Prior art electrodes offer combination structures including a metallic or otherwise conductive support member to which an electrical wire from an associated apparatus may be attached. Some electrodes teach the incorporation of an electrode paste or gel applied directly to the conductive support member to enhance conductivity across the skin-electrode interface.

Other electrodes teach the additional incorporation of an open cellular skin interface pad secured to a conductive support member. This pad, as shown in U.S. Pat. No. 3,817,252, is very often a sponge material and functions to hold or contain an electrolyte solution. The electrolyte solution enhances conductivity across the skin-pad interface. Alternately, this interface pad can be saturated with electrode pastes or gels which will not run or evaporate as readily as electrolyte solutions.

None of these prior art electrodes offer a structure which will maintain constant, efficient and effective electrical transmission for long periods of time without the need for additional electrode paste, gel or solution. Moreover, with these electrodes there is a tendency for the electrolyte film to separate and/or flow to a non-uniform thickness if pressure is applied. Under these conditions, sections of the conductive support member could be exposed to the skin. Local hot spots will results which can cause discomfort to the patient or cause burns to the patient's skin.

These prior art electrodes must be secured to the surface of a patient's skin with medical tape or other securing mediums. Very often an electrode secured in this manner will pull away from the skin creating a partial or total interruption in signal transmission. Further, the adhesives can cause skin irritations.

More recent improvements in the electrode art include composite electrodes using electroconductive tape as the skin interfacing medium. This tape has a film of pressure sensitive adhesive for engaging the skin surface. In these electrodes, the adhesive has been doped with a quantity of electrically conductive particles such as carbon powder as disclosed in U.S. Pat. No. 3,911,906 in order to provide an electrical path to the skin. Alternatively, silver powder may be used instead of carbon powder. This doping can create non-uniform electrical transmission through the adhesive. Moreover, in the presence of large quantities of skin moisture, these adhesives lose their ability to adhere to the skin surface, thus pulling away and drastically changing the electrical characteristics of the electrode.

The present invention provides a composite electrode including a karaya gum mesh work (i.e. matrix) containing a stable electrically conductive substance. The present electrode comprises a three dimensional molecular matrix of karaya gum holding a non-volatile liquid substance with a high enough dielectric constant to hold an adequate number of ionizable molecules (either organic or inorganic) to conduct an electric current with low resistivity. This molecular matrix may take two forms, a molecular mechanical entanglement or a molecular chemical bonding. Illustrative examples of the chemical bonding are:

1. $H+ \rightarrow$ carboxyl
2. Ionic bonding such as $Ca++$ (electrolyte) combined with a carboxyl group
3. covalent bonding such as an ester linkage The present invention provides an electrode with a skin-interface substrate having adhesive properties which will enable the electrode to adhere to the skin without the use of tape or other securing means and which will gain rather than lose adhesiveness in the presence of large quantities of skin moisture. The present electrode has an adhesive skin-interface substrate which is electrically conductive, this conductivity being uniform throughout the substrate. This electrode has a skin-interface substrate which will maintain a uniform thickness and will not separate to expose sections of a conductive support member to the skin. The present skin-interface substrate generally will not dry out under longer periods of use.

SUMMARY OF THE INVENTION

The present invention provides a medical electrode which may include an electrically conductive support and electrical current distribution member. Preferably, this member may be a sheet or layer of metallic or other conductive material having mounted thereon or secured thereto a fastener or other suitable object for securing positive electrical contact between said conductive support member and cables connecting to external electrical equipment. Abutting one side of said support member, and in electrically conductive contact therewith, may be an electrically conductive skin-interface substrate. This substrate may be principally a karaya gum matrix containing a dispersion of an electrically conductive material which may include among these compounds an electrolyte such as sodium-based salts. The electrically conductive material may also include other materials such as carbohydrate, protein or other organic material or inorganic material.

DESCRIPTION OF THE DRAWINGS

The novel features of this invention as well as the invention itself, both as to its organization and method of operation, will be best understood from the following description taken in connection with the accompanying drawings in which like characters refer to like parts, and in which:

FIG. 1b shows an elevation view of the electrode of FIG. 1a;

FIG. 2b shows an elevation of the electrode of FIG. 2a.

DETAILED DESCRIPTION OF THE INVENTION

Medical electrodes are intended for usage as efficient and effective signal transmission mediums between a patient's skin and an electro-medical apparatus. Primary to their operation is a uniform conductivity with low resistivity through the electrode itself and a uniform conductivity and low resistivity across the electrode-skin interface. Uniform conductivity through an electrode is most often interrupted by a non-uniformity in electrode material, while uniform conductivity across the electrode-skin interface is most often interrupted by a separation of some or all of the electrode interfacing material in contact with a patient's skin.

The electrode at hand is intended to have adhesive properties for maintaining contact with the skin, as well as, possessing a certain amount of elasticity for movement with the skin in addition to a uniform configuration for contact with the skin and the passage of uniform current densities to the skin. This electrode is intended to be easily handled and to have a realistic operating life while being non-irritating to the patient.

Figure 1A:
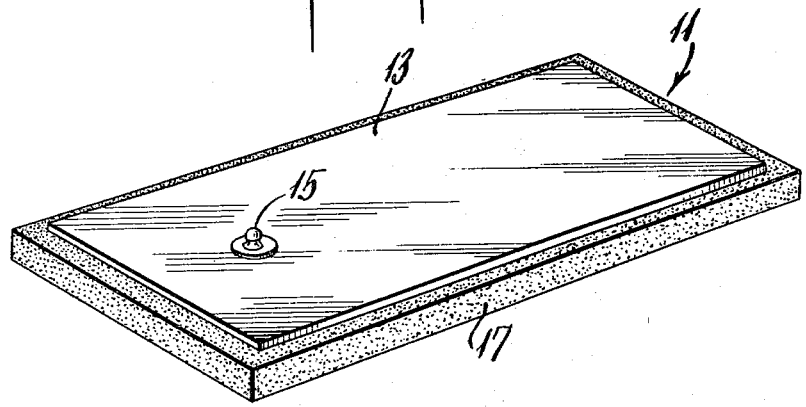
FIG. 1a shows a perspective view of a stimulation electrode.
Figure 1B:
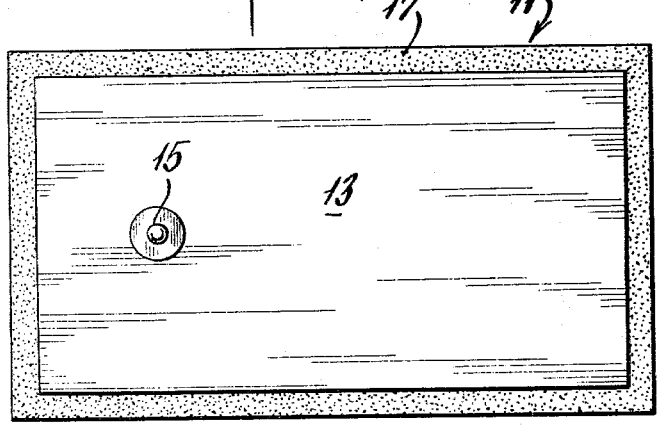

A stimulation electrode configuration 11 is shown in FIGS. 1a and 1b. Included in this configuration 11 is a conductive support and electrical current distribution member 13 which is cut, stamped or otherwise shaped out of a piece of metallic foil. The shape to which this conductive support member 13 is formed will depend upon the particular application in which it is used. Most commonly, as shown in the FIGS. 1a and 1b, this member 13 is rectangular in shape. A suitable conductive support member has been made of aluminum foil 6 mils thick. This foil thickness provides a pliable conductive support member 13 which can easily be pressed to conform to the skin surface of a patient while maintaining sufficient strength to perform the support function. Alternatively, this conductive support and current distribution member 13 may be made of wire mesh, conductive cloth or conductive polymer material. One preferred conductive support member has been prepared of a commercially available conductive cloth produced by Technical Wire Products, Inc. of 129 Dermody St., Cranford, New Jersey under the trademark "Confuzz". The member 13, in any event, is of a material having an appropriate strength and thickness. The material is chosen to yield a pliable yet sufficiently strong member 13.

Secured to the outer surface of the support and distribution member 13 is an electrically conductive swaged snap fastener 15. This fastener 15 is utilized as the electrical connector coupling by which electrical wires may be attached to said distribution member 13. The fastener 15 is rivoted or otherwise mechanically and electrically attached to said support and distribution member and electrically attached to said support and distribution member and may extend perpendicularly from the outer surface of said support and distribution member 13.

Abutting the inner surface of said support and distribution member 13 is an electrically conductive skin-interface substrate 17. This substrate 17 is a layer of material which will be described below.

The substrate 17 is a rectangular sheet of material of uniform thickness of from 1/16 to ½ inch which is cut to shape. As will be discussed below, this substrate 17 has both electrically conductive and adhesive properties, thus, when brought into contact with the support and distribution member 13, intimate contact is maintained with that member 13.

In operation, the electrode 11 is applied with the substrate 17 in direct contact with the skin. The adhesive properties of the substrate 17 eliminate the need for tape or other securing measures to hold the electrode 11 in continuous contact with the skin. As described above, the fastener 15 receives electrical signals from an external apparatus. These signals are conducted into the support member 13 which in turn directly conducts them into uniform substrate 17. In this manner, current densities are uniformly distributed over the area of the substrate 17 in contact with the support and distribution member 13 and in turn, uniformly transmitted to the skin surface in contact with the substrate 17. The substrate is a good electrical conductor and may provide a resistivity of less than 10,000 ohms-meter (as measured using 10 volts alternating current measured peak to peak). Preferably, said resistivity of the substrate is less than 1000 ohms-meter.

Figure 2A:
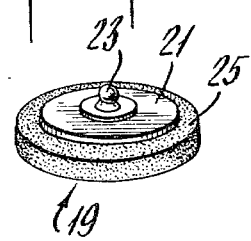
FIG. 2a shows a perspective view of a monitoring electrode.
Figure 2B:
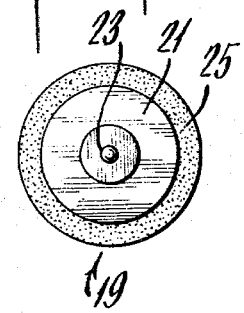

A monitoring electrode configuration 19 is shown in FIGS. 2a and 2b. In configuration 19, a swaged snap fastener 23 is rivoted to the center of the support member 21. Abutting the side of the support member 21 opposite the fastener 23 is a uniform sheet of conductive substrate 25. This substrate 25 is centered on the support member 21 being about 1/16 to ¼ inch thick. The substrate 25 can have identical physical, chemical and electrical properties as the substrate 17 used in the stimulation electrode 11.

In operation, electrical signals present in a patient's body are transmitted across the skin-substrate interface and into the substrate 25 where they are conducted to the fastener 23 and its associated wiring to the monitoring apparatus, respectively.

Primary to the unique structure of the electrodes 11, 19 for eliminating signal artifact, (i.e. a disruption of the signal profile) is the ability of the substrate 17, 25 to adhere to the skin surface when there is motion between the electrode and the skin. The hydrophilic adhesive properties of the electrode enhance the interface transmission of signals. Motion of the electrode produces less of a feedback artifact as there occurs with the use of previous pastes and gels. The structure and composition of the substrate 17, 25 material enables it to possess physical, chemical and electrical properties which reduce feedback artifact under motion by the electrode.

The substrate 17, 25 is a karaya matrix containing an electrolyte or electrically conductive material as previously described. The electrically conductive material may be silver paste or aluminum paste at a 1 to 5 percent level instead of electrolyte.

In its principal embodiment, the substrate 17, 25 is prepared from a dry karaya gum powder and a non-volatile liquid carrying an ionizable salt (organic or inorganic) or a metal finely powdered and held in mechanical suspension by the karaya matrix. The karaya powder and the liquid is mixed and cured. The composition contains sufficient karaya gum to provide a structurally stable element. Typically, the composition will include at least about 10 percent, preferably 30 to 70 percent karaya gum. The remainder of the composition may be an electrically conductive fluid material. The fluid material may be a non-volatile fluid with a high enough dielectric constant to contain an adequate amount of electrolyte for conductance of electrical current and resulting in a low resistivity. The electrolyte may be present in an amount of between 0.005 and 5%. The fluid may be present in an amount of between 30 and 90%. As used herein the terms "parts", "percent" and the like will mean by weight unless otherwise stated. The electrically conductive fluid material is of a character which will form a stable non-weeping member when combined with the karaya gum matrix. The electrically conductive material may include glycerin, propylene glycol, sodium chloride, calcium chloride and water. The following proportions will provide satisfactory substrate members:

|  | Nominal Amounts of Ingredients | Range of Ingredients |
| --- | --- | --- |
| Karaya | 40 gm | 30 to 60 gm |
| Glycerin | 57 gm | 30 to 90 gm |
| Propylene Glycol | 3 cc | 1 to 10 gm |
| Sodium Chloride | .07 gm | .01 to 1.5 gm |
| Water | 3 cc | 1 to 10 gm |
| Calcium Chloride | .06 gm | .01 to 1.5 gm |

The product may be poured into sheets and heated under pressure to 175° F. for a length of time to form sheets of the substrate material. Alternatively, the product may be poured into sheets and cured at room temperature.

Another embodiment of the present electrode includes from 15 to 70 percent aqueous poly acrylic acid (25 percent concentration), from 15 to 45 percent karaya, from 10 to 35 percent water, from 0 to 35 percent isopropyl alcohol and 1 to 3 percent electrolyte. Electrodes were prepared according to the present invention using the six formulations (parts by weight) shown in the following table.

|  | Formula A | Formula B | Formula C | Formula D | Formula E | Formula F |
| --- | --- | --- | --- | --- | --- | --- |
| Aqueous Poly Acrylic Acid (25% concentration) | 67 | 49 | 42 | 33 | 33 | 16 |
| Karaya Powder | 31 | 16 | 28 | 33 | 33 | 33 |
| Water |  | 33 | 14 | 33 |  | 25 |
| Isopropyl Alcohol |  |  | 14 |  | 33 | 25 |
| Sodium Chloride | 2 | 2 | 2 | 2 | 2 | 2 |

The karaya composition is hydrophilic. When one of the substrates 17, 25 comprising this composition is applied to the skin, body moisture, as well as, body salts and heat are absorbed by this composition increasing its tackiness and causing the surface of the material to soften and eventually go into solution if enough heat and water are present. As a result, the substrate will mold into pores and other irregularities in the skin, creating a homogenous mechanical-interlock bond with the skin. Thus, the bonding and elastic properties of the electrode are enhanced as it "ages" in contact with the skin. The electrode, in some instances, may be prepared without electrolyte and when in contact with the skin will pick up enough electrolyte from sweat to be adequately conductive.

The flow condition eliminates air spaces between the skin and the substrate-composition to greatly increase the surface interface which in turn reduces the electric current densities at the skin-substrate interface and makes the density uniform. While the surface portion of the substrate-composition will mold to the skin, the greater portion of its mass will remain intact. The electrical transmission properties of the karaya gum electrode are enhanced as it "ages" in contact with the skin.

A secondary electrical effect is also improved as the electrode "ages". Present during the operation of all electrodes is a battery effect created at the skin interface due to the capacitance across this interface. This battery effect causes some current to circle backward toward its source of flow and create a greater resistivity. In monitoring electrodes, if a second current is applied to the body to cause the heart to beat (i.e. defibrillation) the electrode tends to hold the current and may destroy the electrocardiogram. In the case of the present electrode, there is less tendency to hold this charge and, therefore, the electrocardiogram signal will come back quickly.

The working life of this karaya composition can be extended by reducing body heat and moisture within the electrode and, if used properly, the effective working life may last several weeks. The life may be extended by removing the electrode from the skin and replacing it with another. While off the body, the moisture content will be significantly reduced through evaporation, thus rejuvenating the electrode and extending its working life.

Other materials may be added to form alternate karaya compounds. These other compounds will also enhance the mechanical properties of the original substrate compound by mechanical entanglement cross-linking karaya molecules to varying degrees. These cross-linking materials must form homogenous dispersions and may react with karaya molecules. As an example, such materials may include protein, starch, cellulose, polyvinyl chloride, polyvinyl acetate, urethane, epoxy resins, certain polyesters and calcium salts. The following examples illustrate specific embodiments of the present invention.

EXAMPLE 1

An electrode substrate was prepared according to the present invention by combining 40 grams of karaya gum, 57 grams of glycerin, 3 milliliters of propylene glycol, 0.07 grams sodium chloride, 3 milliliters of water and 0.06 grams of calcium chloride. The mixture was then poured to form a sheet and cured. The substrate was suitable for use as an electrode and had sufficient adhesive properties.

EXAMPLE 2

An electrode substrate was prepared by combining 5 grams of salicylic acid, 10 milliliters of glycerol and 10 grams of karaya. The materials were thoroughly mixed and spread to form a sheet. The resulting sheet was somewhat rubbery and slightly tacky. The sheet was suitable for use as a substrate.

EXAMPLE 3

A substrate was prepared according to the present invention by combining 15 grams of karaya gum and 15 grams sucrose with blending. Then 10 grams of glycerol and an aqueous solution containing 2 grams sodium chloride were added with mixing. This combination was then spread to form a sheet suitable for use as a substrate. The sheet was somewhat granular and medium dark in color. The mixture was homogenous and semi-solid, as well as, slightly tacky.

EXAMPLE 4

An electrode substrate was prepared by combining 10 grams of karaya gum, 15 grams of coal tar and an aqueous solution containing 1 gram sodium chloride. The combination was spread into a sheet following mixing. The sheet was homogenous soft and nontacky. However, it did have an odor from the coal tar. The sheet was considered satisfactory for use as an electrode substrate.

EXAMPLE 5

An electrode substrate was prepared by combining 20 grams karaya gum, 10 milliliters water, 5 milliliters glycerol, an aqueous solution containing 2 grams sodium chloride and 10 grams of sucrose. The mixture was then spread to form a sheet suitable for use as a substrate.

EXAMPLE 6

An electrode substrate was prepared according to the present invention by combining 20 grams of karaya gum with 10 grams of dextrose. The dextrose was in a 70% aqueous solution including 1% sodium chloride. The material was spread to form a sheet which was acceptable for use as an electrode substrate.

EXAMPLE 7

An electrode substrate was prepared by combining 25 grams karaya gum, 45 milliliters of a vinyl acetate ethylene emulsion copolymer (Air Flex 500) and an aqueous solution containg 2 grams sodium chloride. These materials were mixed and then spread to form a sheet suitable for use as a substrate.

EXAMPLE 8

A mixture was prepared including 10 grams karaya gum, 20 grams gelatin, an aqueous solution containing 2 grams sodium chloride and 15 milliliters glycerol. The mixture was prepared by first adding the electrolyte to the gelatin. These materials were then added to the glycerol. The karaya gum was then added to the glycerol. The mixture was spread to form a cohesive sheet which was light tan in color. The sheet was less tacky and resisted tearing. The sheet was suitable for use as a substrate.

EXAMPLE 9

Ten grams of karaya gum were combined with 30 milliliters of egg white and an aqueous solution containing 1 gram sodium chloride to produce a white, amorphous mass. The material is then spread to form a substrate sheet.

EXAMPLE 10

A substrate material was prepared by combining 30 grams karaya gum, an aqueous solution containing 1 gram sodium chloride and 50 milliliters egg white. This combination was thoroughly mixed and spread to form a soft gelatineous sheet.

EXAMPLE 11

Six grams karaya gum were combined with 39 grams egg white and an aqueous solution containing 1 gram sodium chloride thoroughly mixed and spread to form a substrate sheet.

EXAMPLE 12

Thirty grams of karaya gum were combined with 33 milliliters skim milk and an aqueous solution containing 1 gram sodium chloride to produce a dough-like mixture. The mixture was then spread to form a substrate sheet.

EXAMPLE 13

Fourteen grams karaya gum were combined with 52 grams yogurt and an aqueous solution containing 1 gram sodium chloride to produce a bread-like dough. The mixture was spread to form a substrate sheet which was both adhesive and cohesive.

EXAMPLE 14

An electrode substrate was prepared by combining 30 grams karaya gum, 40 grams sorbitol and an aqueous solution containing 1 gram sodium chloride. The mixture was prepared by first combining the electrolyte with the sorbitol and then the karaya gum was added thereto. The resulting material was spread to form a substrate sheet which had good conductivity.

EXAMPLE 15

Thirty grams karaya gum were combined with 30 milliliters of a 70% aqueous sorbitol solution. The solution included an aqueous solution containing 1 gram of sodium chloride. The mixture was then spread to form a sheet and allowed to cure. The sheet was suitable for use as a substrate.

EXAMPLE 16

An electrode substrate was prepared by mixing 5 grams karaya gum with 10 milliliters of glycerol. Then 15 milliliters of polyvinyl acetate copolymer emulsion (Flexbond 150TM) were added with mixing and an aqueous solution containing 1 gram sodium chloride was then added. The mixture was spread to form a sheet suitable for use as a substrate.

EXAMPLE 17

Five grams karaya gum were combined with an aqueous solution containing 1 gram sodium chloride and 30 milliliters polyvinyl acetate copolymer emulsion. The mixture was spread to form a sheet suitable for use as a substrate.

EXAMPLE 18

A mixture including 5 grams karaya gum, 10 milliliters glycerol and aqueous solution containing 1 gram sodium chloride and 5 grams dry milk powder was prepared and spread to form a sheet suitable for use as a substrate.

EXAMPLE 19

A mixture was prepared including 30 parts karaya, 70 parts floor wax (Butcher's TM) and 1 part sodium chloride. The mixture was found suitable for use as an electrode substrate.

EXAMPLE 20

A mixture was prepared including 40 parts karaya, 60 parts acrylic floor polish (Johnson's TM) and 1 part sodium chloride. The mixture was found suitable for use as an electrode substrate.

In the present invention, the karaya gum forms a lattice or matrix which contains a continuous phase of electrically conductive material. The electrically conductive material may be principally a non-volatile solvent and with a high enough dielectric constant to carry an adequate amount of electrolyte. The electrically conductive material will include an electrolyte such as ionizable organic or inorganic salt. The electrically conductive material may include water as the solvent if there is present an adequate amount of carbohydrate, protein, and/or synthetic material to hold the water. Glycerol is also a suitable solvent even without the presence of water. The solvent may be an aqueous solvent or an organic solvent. The organic solvent may be free of water providing it has a high dielectric constant. The term solvent in this instance, is used to indicate a fluid in which the electrolyte can ionize and in which the carbohydrate, protein or polymer may be suspended or dissolved. Illustrations of suitable substrate compositions would include the following parts (by weight):

|   |   | Parts by Weight |
|---|---|---|
| a. | Sorbitol - water (7:3) | 46 to 85 |
|    | Karaya gum | 15 to 54 |
|    | Aqueous saline solution (5% NaCl) | 1 to 3 |
| b. | Molasses | 53 to 85 |
|    | Karaya gum | 15 to 47 |
|    | Aqueous saline solution (5% NaCl) | 1 to 3 |
| c. | Corn syrup | 57 to 85 |
|    | Karaya gum | 15 to 43 |
|    | Aqueous saline solution (5% NaCl) | 1 to 3 |
| d. | Honey | 48 to 85 |
|    | Karaya gum | 15 to 52 |
|    | Aqueous saline solution (5% NaCl) | 1 to 3 |
| e. | Guar - water (10:1) | 80 to 95 |
|    | Karaya gum | 5 to 20 |
|    | Aqueous saline solution (5% NaCl) | 1 to 3 |
| f. | Guar - water (6:1) | 80 to 95 |
|    | Karaya gum | 10 to 20 |
|    | Aqueous saline solution (5% NaCl) | 1 to 3 |
| g. | Potato - water (1:1) | 53 to 85 |
|    | Karaya gum | 15 to 47 |
|    | Aqueous saline solution (5% NaCl) | 1 to 3 |
| h. | Egg white | 60 to 88 |
|    | Karaya gum | 12 to 40 |
|    | Aqueous saline solution (5% NaCl) | 1 to 3 |
| i. | Yogurt | 50 to 85 |
|    | Karaya gum | 15 to 50 |
|    | Aqueous saline solution (5% NaCl) | 1 to 3 |
| j. | Skim milk | 40 to 85 |
|    | Karaya gum | 15 to 60 |
|    | Aqueous saline solution (5% NaCl) | 1 to 3 |
| k. | Polyvinyl acetate copolymer emulsion | 70 to 90 |
|    | Karaya gum | 10 to 30 |
|    | Aqueous saline solution (5% NaCl) | 1 to 3 |
| l. | Vinyl acetate ethylene emulsion | 70 to 90 |
|    | Karaya gum | 10 to 30 |
|    | Aqueous saline solution (5% NaCl) | 1 to 3 |
| m. | Polyvinyl acetate copolymer | 60 to 80 |
|    | Karaya gum | 10 to 20 |
|    | Glycerin | 10 to 20 |
|    | Aqueous saline solution (5% NaCl) | 1 to 3 |
| n. | Polyvinyl acetate copolymer/ vinyl acetate ethylene emulsion (2:1 to 3:1) | 70 to 90 |
|    | Karaya gum | 10 to 30 |
|    | Aqueous saline solution (5% NaCl) | 1 to 3 |

The substrate compound should be non-reactive with the patient's skin. Efforts should be directed to maintain a proper pH and to add only hypo-allergenic compounds to the mixture. The compound can be subjected to inhibit microbial growth but such radiation should be below 2.5 mega rads gamma radiation.

In the present invention, the electrode may be prepared including approximately 5 to 60 parts karaya, approximately 35 to 80 parts glycerin and 1 to 5 parts finely divided metal. The metal may, for example, by aluminum or silver. In a further embodiment, the electrode may be made using 20 to 60 parts karaya and 40 to 80 parts glycerin. Such electrode may be made without electrolyte and pick up sufficient electrolyte from the skin of the patient.

Additional variations may also be made in the electrode. An open cell sponge or similar material may be impregnated with the karaya compound. This sponge could be used to act as a support structure for shaping the karaya compound sheet for a particular use.

For other applications, the electrical fastener 15 and the method of making an electrical connection to the electrode could be changed. Instead of the fastener 15, a wire could be attached to the support member 13 in a "pig-tail" arrangement for mating an electrical cable away from the electrode structure itself. This pig-tail connection to the electrode would permit connecting the electrode without the possibility of disturbing its position on the skin.

It is to be recognized that various modifications may be made in the specific illustrations while still providing a suitable substrate according to the present invention.

What is claimed is:

1. An electrode for establishing electrical connection to a patient's skin, comprising:
   an electrically conductive backing and current distribution member;
   electrical terminal means attached to said member, said terminal means being adapted for connection of the electrode to an electrical wire; and
   a substrate attached to said backing and current distribution member for interfacing with the patient's skin, said substrate comprising a homogeneous material having adhesive properties for securing the electrode to the skin, said substrate being sufficiently pliant to permit formation of the shape of the electrode to the body contours, said substrate being sufficiently firm to prevent penetration of the body contours through the substrate thereby preventing contact of the backing member with the skin, and said substrate being uniformly conductive thereby providing a homogeneous conducting surface to the skin, said substrate comprising a karaya gum matrix, said matrix supporting an electrically conductive fluid, said fluid comprising an organic fluid and being a continuous phase.

2. The electrode of claim 1 wherein said karaya gum is present in said substrate at a level at least about 10% by weight.

3. The electrode of claim 1 wherein said substrate includes an electrolyte and wherein said electrically conductive fluid is a non-volatile fluid with a high enough dielectric constant to contain an adequate amount of electrolyte to conduct electricity so that the resistivity is low.

4. The electrode of claim 3 wherein said electrically conductive fluid further includes at least one member of the group consisting of carbohydrates, proteins and polymers.

5. The electrode of claim 4 wherein said carbohydrate is a member of the group consisting of monosaccharides, disaccharides, and polysaccharides.

6. The electrode of claim 4 wherein said protein is a member of the group consisting of milk, gelatin, egg white, albumin and yogurt.

7. The electrode of claim 4 wherein said polymer comprises polyvinyl acetate copolymer emulsion.

8. The electrode of claim 4 wherein said electrically conductive fluid further includes vinyl acetate ethylene emulsion.

9. The electrode of claim 8 wherein said electrically conductive fluid also includes polyvinyl acetate copolymer emulsion.

10. The electrode of claim 3 wherein said substrate has a resistivity of less than 1000 ohms-meter.

11. The electrode of claim 3 wherein said substrate has a resistivity of less than 10,000 ohms-meter.

12. The electrode of claim 3 wherein said electrolyte comprises an inorganic salt.

13. The electrode of claim 3 wherein said electrolyte comprises an ionizable organic salt.

14. The electrode of claim 3 wherein said non-volatile fluid is an organic solvent.

15. The electrode of claim 14 wherein said substrate is substantially free of water.

* * * * *

UNITED STATES PATENT AND TRADEMARK OFFICE
CERTIFICATE OF CORRECTION

PATENT NO. : 4,274,420
DATED : June 23, 1981
INVENTOR(S) : Alan C. Hymes

It is certified that error appears in the above—identified patent and that said Letters Patent is hereby corrected as shown below:

Column 1, line 21, should read --surfaces[.], [W]while--;
Column 4, lines 3-5, delete "and electrically attached to said support and distribution member--, second occurrence;
Column 4, line 12, "1/2" should be --1/4--;
Column 4, line 16, delete "," and insert --;--;
Column 6, line 4, "homogenous" should be --homogeneous--;
Column 7, line 22, after "homogenous" insert --,--;
Column 7, line 47, "containg" should be --containing--;
Column 7, line 46, entry should read "Air Flex 500$^{TM}$";
Column 8, line 51, entry should read "Flexbond 150$^{TM}$";
Column 9, line 4, should read "Butcher's$^{TM}$";
Column 9, line 10, should read "Johnson's$^{TM}$";
Column 10, line 19, "by" should be --be--;
Column 12, line 1, "4" should be --3--.

Signed and Sealed this

Sixteenth Day of February 1982

[SEAL]

*Attest:*

GERALD J. MOSSINGHOFF

*Attesting Officer*     *Commissioner of Patents and Trademarks*